United States Patent [19]

Krevolin et al.

[11] Patent Number: 5,362,625
[45] Date of Patent: Nov. 8, 1994

[54] METHODS AND COMPOSITIONS FOR ENZYME COMPLEMENTATION ASSAYS USING THE OMEGA REGION OF β-GALACTOSIDASE

[75] Inventors: Mark Krevolin, El Cerrito; David Kates, Concord, both of Calif.

[73] Assignee: Microgenics Corporation, Concord, Calif.

[21] Appl. No.: 67,342

[22] Filed: May 25, 1993

Related U.S. Application Data

[63] Continuation of Ser. No. 700,549, May 15, 1991, abandoned.

[51] Int. Cl.$^5$ .................. C12Q 1/34; G01N 33/535
[52] U.S. Cl. ......................... 435/7.6; 435/18
[58] Field of Search ................. 435/7.6, 18

[56] References Cited

U.S. PATENT DOCUMENTS 4,378,428  3/1983  Farina et al. ..................... 435/7
4,708,929  11/1987  Henderson ....................... 435/7

FOREIGN PATENT DOCUMENTS

90/13569  11/1990  WIPO .

OTHER PUBLICATIONS

Ullmann, A. and Perrin, D. "Complementation in β-galactosidase," in *The Lactose Operon* (ed. J. R. Beckwith and D. Zipser.), pp. 143–172, Cold Spring Harbor Laboratory, Cold Spring Harbor, N.Y. (1970).
Celada, F., Ullmann, A. and Monod, J. "An Immunological Study of Complementary Fragments of β-Galactosidase" *Biochemistry*, vol. 13 (27), pp. 5543–5547 (1974).
Welphy, et al., *J. Biol. Chem.*, 256:6804 (1981).
Langley, et al., *Biochemistry*, 15:4866 (1976).
Langley, et al., *Proc. Natl. Acad. Sci. USA*, 72(4):1254.

*Primary Examiner*—David Saunders
*Attorney, Agent, or Firm*—Cooley Godward Castro Huddleson & Tatum

[57] ABSTRACT

The use of omega-acceptor and omega-donor polypeptides (comprising about two-thirds and one-third of the β-galactosidase molecule amino and carboxyl termini, respectively), prepared by recombinant DNA techniques, DNA synthesis, or chemical polypeptide synthesis techniques, which are capable of interacting to form an active enzyme complex having catalytic activity characteristic of β-galactosidase, is described along with improved methods and novel compositions for enzyme complementation assays for qualitative and quantitative determination of a suspected analyte in a sample.

8 Claims, 5 Drawing Sheets

METHODS AND COMPOSITIONS FOR ENZYME COMPLEMENTATION ASSAYS USING THE OMEGA REGION OF β-GALACTOSIDASE

CROSS REFERENCE TO RELATED APPLICATIONS

This application is a continuation of U.S. application Ser. No. 07/700,549, filed May 15, 1991 and now abandoned.

FIELD OF THE INVENTION

This invention relates to enzyme-labelled reagents and to assays that use enzyme activity as a marker indicating the presence of an analyte and is particularly directed to improved methods and novel compositions for qualitative and quantitative analysis of analytes by enzyme complementation assays using β-galactosidase.

BACKGROUND OF THE INVENTION

Figure 1:
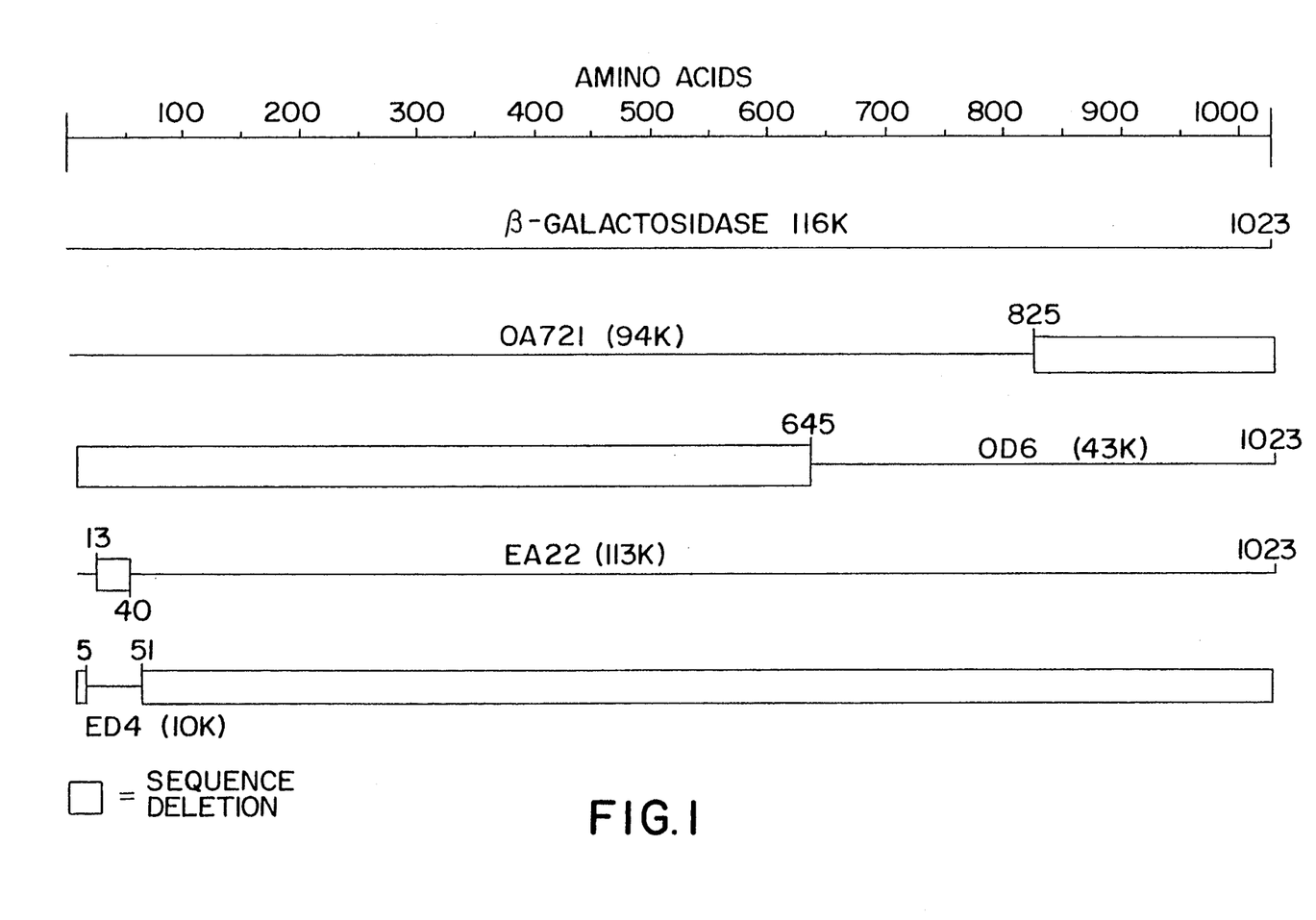
FIG. 1 schematically represents the β-galactosidase polypeptide, together with selected deletion mutants.

The enzyme β-galactosidase has for a long time found wide use in enzyme-linked immunosorbent assays (ELISA) (Engvall and Perimann, 1971, *Immunochemistry* 8:871) and homogeneous substrate labeled assays (Burd et al., 1977, *Clin. Chem.* 23:1402). In addition, β-galactosidase forms the basis of a widespread genetic system for DNA cloning and DNA sequencing (Messing, 1983, *Methods of Enzymology* 101:20).

β-Galactosidase is a tetrameric protein having a molecular weight (MW) of about 540,000 daltons. The four identical monomers consist of 1023 amino acids, each with a MW of 116,000 daltons. The monomeric protein, as shown in FIG. 1, is divided into three regions: (1) the N-terminus proximal segment (the α-region), (2) a middle region, and (3) a C-terminus distal segment (the ω-region).

Mutant polypeptides derived from β-galactosidase are known which can complement or spontaneously restore enzyme activity when added to extracts of appropriate β-galactosidase negative mutants. This phenomenon is known as intracistronic complementation. When complementation involves a deletion or chain interruption in the α-region, the process is referred to as α-complementation. An example of α-complementation is provided by the M15/CNBr2 complementation system. The M15 mutant polypeptide lacks amino acids 11–41 of β-galactosidase and exists in solution as an enzymatically inactive dimer. A polypeptide derived from β-galactosidase by cyanogen bromide cleavage, denoted the CNBr2 peptide (CNBr2), consists of amino acids 3–92. CNBr2, when mixed with the dimer M15, promotes spontaneous reconstruction of the β-galactosidase tetramer with full enzymatic activity (Langley and Zabin, 1976, *Biochemistry* 15:4866). The M15 peptide is therefore known as an β-acceptor and CNBr2 as an β-donor.

While this represents a well-studied complementing system, CNBr2 can also serve as an α-donor for the M112 dimer, a deletion of amino acids 23–31 within β-galactosidase (Lin, Villarejo and Zabin, 1970, *Biochem. Biophys. Res. Common.* 40:249; Celeda and Zabin, 1979, *Biochem.* 18:404; Welphy, Fowler and Zabin, 1981, *J. Biol. Chem.* 256:6804; Langley et al., 1975, *Proc. Natl. Acad. Sci. USA* 72:1254). In the example of complementation of M15 by CNBr2, amino acid sequences 3–10 and 42–96 are both present in duplicate in the enzymatically inactive complex.

Intracistronic complementation also occurs at the C-terminus of β-galactosidase (the ω-region). An early publication that describes structural studies related to complementation of β-galactosidase in the carboxy-terminal region is M. E. Goldberg, *The Lactose Operon*, Cold Spring Harbor Laboratory, 1970. The most widely studied example is the X90-acceptor peptide that deletes that last 10 amino acids, 1013–1023. The X90 peptide exists as a monomer and can be complemented by CNBr24, a cyanogen bromide digestion product of β-galactosidase consisting of amino acids 990–1023, to reform enzymatically active tetramer (Welphy et al., 1980, *Biochem. Biophys. Res. Common.* 93:223).

A number of patent applications and patents relating to complementation assays have arisen out of the laboratories of the present inventors. Those applications that are directed to β-galactosidase enzyme donors and acceptors are U.S. application Ser. No. 666,080, filed Oct. 29, 1984, now abandoned; U.S. application Ser. No. 721,267, filed Apr. 8, 1985, now U.S. Pat. No. 4,708,929; U.S. application Ser. No. 788,370, filed Oct. 22, 1985, now U.S. Pat. No. 5,120,653; U.S. application Ser. No. 347,679, filed May 5, 1989, now abandoned; U.S. application Ser. No. 410,996, filed Sep. 22, 1989, now abandoned; and PCT application PCT/US90/02491, filed May 4, 1990, now pending as an international PCT application designating the US. All of these patents and patent applications are herein incorporated by reference. In particular, several of these earlier patents and applications disclose the complete genetic and amino acid sequence of the beta-galactosidase enzyme.

SUMMARY OF INVENTION

The present invention provides improved methods and novel compositions for enzyme complementation assays using variants in the ω-region of β-galactosidase for quantitative analysis of analytes of both high and low molecular weight (e.g., 150–300,000 daltons MW) in high (e.g., $10^{-15}$ M) sensitivity. The assays are referred to collectively as OPRA assays based on "omega-complementation." However, they are not to be confused with the previously known complementation assays described using the omega-region of β-galactosidase, as the prior assays used a different part of the omega-region.

Omega complementation involves reassembly to an active β-galactosidase in a manner similar to that previously done for other β-galactosidase variants. As discussed above, most previous β-galactosidase complementation assays involved reassembly of polypeptides formed by breaking the β-galactosidase molecule in the α-region (some of the fragments overlapped, in addition to those that were exactly complementary); such reassembly was referred to as α-complementation, Omega complementation, in contrast involves reassembly of the carboxyl terminus of β-galactosidase. The two complimentary polypeptide fragments are known as the omega-donor and the omega-acceptor molecules. As used in this specification, the "donor" molecule is the smaller of the two molecules which assembles with the larger "acceptor" molecule. It has been determined that the omega-donor molecule is particularly effective when it is approximately ⅓ of β-galactosidase and contains the carboxyl terminus. The omega-acceptor contains the remaining ⅔ of β-galactosidase, with some overlap being possible. By using complementary fragments at the omega-end of β-galactosidase, a diagnostic assay with a number of useful characteristics that is capable of measuring low concentrations of analyte can be obtained. For example, the omega-donor molecule has a stable, folded structure that is close to or identical with the structure of this domain of the intact β-galactosidase molecule. This feature allows a fast kinetic interaction of complementary molecules with no lag time associated with conformational changes. The stability of the omega-donor structure also makes it possible to purify this molecule intact without coexpression and later removal of its complementary molecule (the omega-acceptor). This allows increased efficiency of production of the donor molecule in comparison to the donor molecule used in α-complementation. The omega-donor molecule of the invention further retains its structure in solution, thus minimizing problems with reagent stability which, although they can be overcome with proper use of stabilizing reagents, increases the complexity and cost of α-complementation.

A particularly useful characteristic of omega-complementation arises from the heightened sensitivity of the carboxyl terminus of β-galactosidase to primary structural changes compared to similar changes in the amino terminus. Steric inhibition also appears to be more prominent in the carboxyl terminus. These characteristics allow a faster and more complete inhibition of complementation in assays involving the omega-region; accordingly, assays using omega-complementation have a lower signal-to-noise ratio and increased sensitivity when compared to α-complementation.

According to the present invention, polypeptides useful in omega-complementation are produced by recombinant DNA techniques or by chemical polypeptide synthesis techniques. As used herein, the term "polypeptide" is inclusive of peptides and proteins. The polypeptides themselves are enzymatically inactive; however, when reacted together in aqueous medium they associate to form a catalytically active enzyme via complementation. β-Galactosidase is an especially favored enzyme for use in diagnostic assays because it has several substrates that are detectable using spectrophotometric and fluorometric methods, it has shown utility in previous commercial immunoassays, it can be measured at extremely low concentrations, and it is well characterized genetically. By creating enzymatic activity from components that produce insignificant background activity, a high signal-to-noise ratio can be achieved.

The novel polypeptides used in the improved assays of the present invention encompass (a) fusion proteins in which analyte is fused to polypeptide, which can be the product of recombinant genes containing sequences coding for analyte and polypeptide; (b) polypeptides genetically engineered for optimal coupling with analytes; (c) polypeptides chemically synthesized for optimal coupling with analytes; and (d) polypeptides genetically engineered or chemically synthesized for improved stability to such environmental factors as oxidation, heat, pH, enzymatic degradation, and the like.

Thus methods are described for creating an immunoassay based upon the use of recombinant DNA techniques or chemical polypeptide synthesis technique to provide appropriate polypeptides that (1) are capable of complementation, (2) can be systematically adjusted to their equilibrium constant of reassociation, (3) are capable of interacting with specific binding proteins, and (4) can, by interaction with specific binding proteins, control the formation of active enzyme having the activity characteristic of β-galactosidase.

The genetically engineered and chemically synthesized polypeptides of this invention offer distinct advantages over other complementing enzyme systems, including prior omega- and α-complementation systems using β-galactosidase. Polypeptides produced by recombinant DNA techniques can be made in large quantity at low cost, can be easily purified to homogeneity and can be made of any size and sequence. Chemically synthesized polypeptides, particularly those that are relatively small in amino acid length, can be made in large yield in unlimited sequence variation. Either preparative technique provides for manipulation of amino acid sequence, leading to polypeptides of improved coupling chemistries, enzymatic reaction kinetics, enzymatic assay sensitivity and/or stability.

The present invention also entails kits for carrying out an assay according the methods of the invention.

BRIEF DESCRIPTION OF THE FIGURES

The invention may be more fully understood by reference to the following detailed description of the invention, to examples of specific embodiments of the invention, and to the appended drawings in which.

DETAILED DESCRIPTION OF THE INVENTION

The present invention comprises improved assays for a variety of analytes employing enzymatically inactive polypeptides prepared using recombinant DNA techniques or chemical polypeptide synthesis techniques which, when incubated together in aqueous medium, form an active β-galactosidase enzyme complex by the process of complementation. Specifically, the techniques involve complementation in the omega-region of β-galactosidase between two polypeptide fragments of the whole β-galactosidase molecule formed by a break in the primary structure of β-galactosidase in the omega-region. In some cases the two fragments are not strictly complementary so as to form an exact β-galactosidase amino acid sequence without gaps or overlaps; both gaps and overlaps are possible as long as the resulting fragments can assemble into an active β-galactosidase molecule. The two polypeptides are termed (1) an omega acceptor and (2) an omega donor. As previously discussed, the acceptor molecule is the larger of the two fragments and normally contains about two-thirds of the amino acid sequence of natural or modified, full-length β-galactosidase. The donor molecule is the smaller fragment containing the remaining one-third (approximately) of the amino acid sequence; the donor molecule is derived from the C terminus of the β-galactosidase molecule.

In general, the acceptor molecule will be a polypeptide having an amino acid sequence from 600 to 1012 amino acids in length, more preferably 700 to 850 amino acids in length, that is substantially identical to the amino acid sequence at the amino terminus of β-galactosidase (i.e., amino acids 1 to x as β-galactosidase is normally numbered, where x is the length of the polypeptide). The β-galactosidase can be derived from any source, but a bacterial source is preferred, particularly E. coli. Other sources include various Bacillus species; thermostable β-galactosidase is available from Streptomyces coelicolor and various Thermus species. Numerous bacterial strains capable of producing β-galactosidase (and thus containing genetic information encoding β-galactosidase for manipulation as described herein are publicly available from depositories such as the American Type Culture Collection, Rockville Md., USA. The donor molecule will be a polypeptide having an amino acid sequence from 10 (preferably 12) to 500 amino acids in length, preferably 300 to 450 amino acids in length, that is substantially identical to the amino acid sequence at the carboxyl terminus of β-galactosidase (i.e., amino acids y to 1023, where y is the position of the first amino acid in the β-galactosidase sequence).

By definition, a polypeptide that is "substantially identical" to a terminal sequence of β-galactosidase (either end) includes but is not limited to a sequence that begins at the natural terminal amino acid and continues without deletions, insertions, or modifications of the natural sequence for the indicated number of amino acids. Such unmodified sequences are referred to as "identical" sequences and are preferred. Typical modifications that occur in "substantially identical" sequences include substitutions of one amino acid for another (usually done to provide a functional group for attachment of another component of the assay, as described below), modifications of a natural amino acid (such as capping of sulfhydryl groups to prevent crosslinking via oxidation or other processes), deletions, and insertions. Except for deletions at the very terminus of the β-galactosidase sequence (i.e., the amino terminus for the acceptor molecule and the carboxyl terminus for the donor molecule, which are referred to as non-complementing termini), alterations from the natural sequence of a donor or acceptor molecule are preferably limited to no more than 20 amino acids (total of deletions, insertions, substitutions, and modifications), more preferably no more than 12 amino acids, even more preferably no more than 7 amino acids, most preferably 3 or fewer. Deletion from a non-complementing terminus is preferably limited to 12 or fewer amino acids, more preferably 5 or fewer.

"About," when referring to the length of a polypeptide fragment, preferably means within 10% (of the indicated number of amino acid residues), more preferably within 5%, even more preferably within 2%. For example, as sequence of "about 300 amino acids" is preferably from 270 to 330 amino acids in length, more preferably from 285 to 315 amino acids in length, even more preferably from 294 to 306 amino acids in length. "About" includes the possibility of at least one amino acid difference in length, even for short polypeptides. A sequence indicated to be "about" a particular length is preferably of the exact indicated length.

The two complementing fragments can contain an overlap region where up to 300, preferably 200 or fewer amino acids, are duplicated when complementation occurs. Gaps in the β-galactosidase sequence can occur on complementation, but are not preferred.

Whether any particular modification from a natural (i.e., "identical") donor or acceptor sequence or whether any two complementing molecules with gaps or overlap regions will be effective can readily be tested by preparing the desired modification as a test molecule and combining the test molecule with a complementary donor or acceptor. Measurement of β-galactosidase activity readily provides data on the effectiveness of any particular modification or combination. Activity equal to that of natural β-galactosidase is not required, as omega complementation assays provide other advantages as described herein. However, modifications and combinations that achieve high activity upon complementation are naturally preferred over modifications and combinations that show lesser activity.

Particularly preferred is a donor polypeptide that comprises about 378 amino acids counting from the carboxyl terminus of β-galactosidase. A preferred acceptor polypeptide comprises about 787 amino acids from the amino terminus of β-galactosidase.

According to the methods of the present invention, recombinant DNA techniques may be used to prepare one or both polypeptides required for complementation. DNA synthesis techniques are applied to the preparation of gene sequences coding for polypeptides of a variety of lengths. Omega donors and omega acceptors are prepared by those techniques. Chemical polypeptide synthesis techniques are generally applied to the preparation of polypeptides that are relatively short in amino acid length. For this reason, chemical techniques (when used) are best suited for the synthesis of donors molecules of the β-galactosidase system, since the donors molecules are typically short in amino acid sequence compared to the acceptors. Of course, this is not to say that functional acceptors cannot be prepared by peptide synthesis techniques.

As defined herein, an omega acceptor molecule (sometimes referred to as an acceptor fragment) is an enzymatically inactive polypeptide produced by a deletion mutant of the β-galactosidase gene, which when combined with an omega donor is capable of forming β-galactosidase by the process of complementation. All omega acceptors constructed herein are polypeptides constructed with deletions in the omega-region of the β-galactosidase gene encoding the C-terminus of the β-galactosidase protein. Some of these omega acceptors have been further manipulated through modification of amino acid residues in the primary sequence to provide for greater stability or ease of coupling to analyte analogues.

As defined herein, a donor molecule (or fragment) is an enzymatically inactive polypeptide comprised of two domains: (a) an omega-donor domain containing an amino acid sequence capable of combining with an acceptor to form active enzyme, and (b) an analyte domain capable of interacting with an analyte-binding protein. The analyte domain is either (1) an analyte-coupling domain through which attachment to various analytes or analyte analogues can be accomplished, or (2) a protein domain which itself functions as an analyte analogue. In fact, it will be recognized by those skilled in the art that one donor domain and the analyte domain are merely regions of the complete donor polypeptide so designated for ease of reference. The analyte domain refers to that portion of the donor molecule where the analyte is attached or which functions as an analyte analogue, while the donor domain is the remainder of the donor molecule, especially that part which is necessary for complementation.

As defined herein, an analyte-coupling domain comprises either the natural sequence of amino acids in β-galactosidase at the point of analyte attachment or it comprises amino acids inserted or substituted into the polypeptide to provide convenient sites for the covalent coupling of analytes. The chemical coupling sites are most frequently sulfhydryl or amino groups associated with cysteine or lysine residues, but can be any appropriate chemically reactive group of any amino acid which is capable of binding to analyte without interfering with (a) the process of complementation or (b) interaction of the analyte with an analyte-binding protein. The location of the chemically reactive group can be altered to meet the steric hindrance requirements of the assay.

As defined herein, a protein domain comprises a protein antigen or an immunoreactive group of an antigen (epitope) that is covalently attached by an amide bond as part of the principal amino acid sequence of the donor molecule, usually at the carboxyl terminus. For example, antigens such as tumor, bacterial, fungal, viral, parasitic, mycoplasmal, histocompatibility, differentiation and other cell membrane antigens, pathogen surface antigens, toxins, allergens, drugs and any biologically active molecules including but not limited to gonadotropin hormone, ferritin, or any other antigenic molecule corresponding to or analogous to an analyte are possible. As recognized by those skilled in the art, donor molecules wherein the analyte domain is a protein domain are also termed "fusion proteins." The term "fusion protein" as used herein is applicable to those enzyme donors comprised of an omega-donor domain and a protein domain specifying immunoreactive epitopes of a protein antigen. It is, of course, possible for the protein domain to comprise a non-immunoreactive protein or fragment thereof capable of interacting with an analyte binding protein other than an antibody. The protein domain of fusion proteins obviates the need to covalently couple an analyte to the analyte domain as is necessary where the analyte domain is an analyte-coupling domain. This is because the protein domain portion of a fusion protein is, in essence, an analyte (or, at least, a close analogue of one) capable of competing with free analyte for analyte-binding proteins.

As in any enzyme assay for analyte contained in a sample of medium, an analyte-binding molecule (generally but not necessarily a protein) included as a reagent in the assay mixture must competitively interact or combine with both free analyte and with analyte coupled to or fused as part of the analyte domain of the omega donor. Interaction of the analyte-binding molecule with analyte coupled to or fused with the omega donor (hereinafter termed "omega-donor conjugate") must inhibit the process of complementation of omega donor and omega acceptor. As defined herein, analyte-binding proteins include specific antibody molecules including conventional polyclonal and monoclonal antibodies (and fragments thereof), receptors, transport proteins, lectins, and other binding proteins, including but not limited to avidin, and thyroxine binding globulin. As defined herein, the broader term analyte-binding molecule encompasses proteinaceous substances such as glycoproteins and lipoproteins, as well an non-proteinaceous substances such as carbohydrates (e.g., for binding with lectins, when the lectin is an analyte) and nucleic acids (e.g., for binding with target nucleic acids, as in a hybridization assay). Because proteins are generally used as analyte-binding molecules in most assays, the phrase "analyte binding protein" will be used for the remainder of this specification, it being recognized that non-proteinaceous binding molecules can be used where appropriate.

The enzyme assay methods of the present invention are based upon competitive binding mechanisms. According to the present invention, a known amount of an omega-enzyme donor of the β-galactosidase system comprising a coupled or fused analyte (or an analogous analyte derivative) of interest (i.e., omega-donor conjugate) is combined with a known amount of a specific analyte-binding protein or other binding molecule and a known amount of an omega acceptor capable of complementation with the omega enzyme donor. Competition between the analyte domain of the omega-donor conjugate and free unknown analyte in the sample for the known amount of specific analyte-binding protein allows the omega-donor conjugate to remain free so that it binds to the omega acceptor. The association of omega-donor conjugates and omega acceptor results in the formation of a catalytically active enzyme complex, thus modulating the amount of β-galactosidase enzyme activity detectable in the sample. As a result, the amount of free analyte in the sample is determined as a direct function of the measurable enzyme activity. Enzyme activity is measured by monitoring the rate of substrate conversion by the enzyme catalyzed reaction by any of a variety of techniques including, but not limited to spectrophotometric and fluorometric methods.

The competitive reactions of the present assay may be represented as follows, wherein the analyte, omega-donor conjugate, omega acceptor, analyte-binding protein, and β-galactosidase enzyme are respectively represented by A, OD-A, OA, Abp, and E. A binding complex is indicated X - Y (a bond would be shown X—Y).

(1)

(2)

where $k_{2a}$ and $k_{2d}$ represents constants of association and disassociation of omega-donor conjugate and analyte-binding protein;

(3)

where $k_{3a}$ and $k_{3d}$ represent constants of association and disassociation of omega-donor conjugate and enzyme-acceptor polypeptides.

Binding of the analyte-binding protein (Abp) to an accessible determinant on the omega-donor conjugate (OD-A) inhibits the complementation reaction such that the omega acceptor remains an inactive dimer.

Thus, reaction (2)

competes with $$OD\text{-}A + OA \rightarrow E.$$

Using known concentrations of Abp, OD-A, and OA, the activity of the complexed β-galactosidase [E] will be directly proportional to the unknown concentration of free analyte of interest in the sample.

As in conventional enzyme assays, for satisfactory sensitivity, formation of active enzyme by complementation of the omega-donor conjugate coupled to analyte-binding protein together with the omega acceptor must be minimal. Stated in other words, either both reactions (4) and (5) below must proceed only minimally or not at all.

(4) $OD\text{-}A - Abp + OA \rightarrow OD\text{-}A - Abp - OA$ $$S \xrightarrow{OD-A - Abp - OA} P \quad (5)$$

wherein OD-A, Abp, and OA are as described above, and substrate and product for the reaction catalyzed by active enzyme (E) are respectively S and P.

A useful component for designing a particular assay with satisfactory sensitivity is the relationship among (1) the association constant for the omega-donor conjugate and omega acceptor ($k_{3a}$); (2) the concentration of specific analyte-binding protein ([Abp]); (3) the association constant for specific analyte-binding protein and omega-donor conjugate ($k_{2a}$); and the concentration of omega acceptor ([EA]).

The components of the enzyme complementation assays of the present invention may be packaged in a kit either in aqueous medium or in lyophilized form. Each component or reagent can be packaged either separately or with another component so long as the sensitivity of the assay is not altered and the component is not adversely affected.

According to a preferred aspect of the present invention, improved complementation assays are achieved by use of omega donors and omega acceptors prepared using recombinant DNA techniques and/or chemical polypeptide synthesis techniques in which the break in the β-galactosidase primary structure occurs in the omega-domain instead of the α-domain previously used and in which other modifications in the amino acid sequence of β-galactosidase also occur. Such techniques permit improved chemistry for covalent coupling between omega donors and analytes via insertion or substitution of amino acids having the appropriate reactive groups, e.g., amino, sulfhydryl, carboxyl, etc. Such techniques permit more precise control of the association constant between omega acceptor and omega donor by systematically determining the amino acid sequence of the complementing polypeptides. Additionally, such techniques yield inexpensive, reliable sources of these polypeptides.

According to one embodiment of the present invention, enzyme donors having an omega-donor domain and an analyte domain are prepared by the use of recombinant DNA techniques to improve the chemistry for coupling an analyte to the analyte domain. These omega donor polypeptides provide convenient coupling sites for the covalent attachment of analyte at varying distances from the omega-donor domain sequence required for complementation.

To obtain omega-donor polypeptides of the type containing an analyte-coupling domain, a plasmid containing genetic information encoding β-galactosidase can be cleaved at different sites in the omega-region of the β-galactosidase gene using a variety of restriction enzymes. Numerous publicly available sources of such genetic material are available through depositories such as the American Type Culture Collection, Rockville Md., USA. Examples include ATCC deposit numbers 9637, 15223, 15224, 21666, 27737, and 31382. See FIG. 2 for a description of plasmid 230, a plasmid that encodes β-galactosidase lacking a portion of the N-terminus. For example, cleavage at the Bam and Sac sites of p230 (and other similar plasmids encoding β-galactosidase) excises the portion of the plasmid encoding the remaining N-terminus amino acids of β-galactosidase. The Bam and Sac cleavage sites can then be linked using a synthesized DNA linker containing Bam and Sac ends. The resulting re-ligated plasmid contains the carboxyl-terminus ⅓ of β-galactosidase.

Additionally, a plasmid may be genetically engineered to place the omega-donor sequence under regulatory control of a temperature inducible promotor or other type of inducible promotor. This may be accomplished, for example, using a λPR promotor in combination with a λ repressor protein (coded by the λ CI gene), which is temperature sensitive, and allows for temperature induction of protein expression. The λ mutant gene, codes for a temperature sensitive repressor protein, which is inactive at temperatures greater than 40° C.

According to another embodiment of the present invention, enzyme donors having an omega-donor domain and an analyte-coupling domain are prepared by the use of chemical polypeptide synthesis techniques to improve the chemistry for coupling an analyte to the analyte domain. These omega-donor polypeptides provide convenient coupling sites for the covalent attachment of analyte at varying distances from the omega-donor domain sequences required for complementation. Chemical peptide synthesis techniques may also be employed to prepare enzyme donors comprising an omega-domain and a protein domain. Omega-donor peptides are synthesized on an automated peptide synthesizer by standard synthetic techniques. Briefly, a protected amino acid representing the carboxyl terminus amino acid of the desired peptide is attached to cross-linked polystyrene beads. The resin beads function as a solid phase to which additional amino acids may be coupled in a step-wise manner. The peptide is generated by growing the chain sequentially from the carboxyl-terminus to the N-terminus. The solid phase facilitates driving the reaction rapidly to 100% completion by the use of excess reagents. The excess reagents can then be easily washed away. Upon completion of the synthetic steps, the peptide is removed from the resin and purified.

The omega-enzyme-donor polypeptides prepared according to the present invention are genetically engineered or chemically synthesized to provide sulfhydryl, amino or carboxyl groups sufficiently removed from the N-terminus so that the analytes are covalently attached to these groups without interfering with the ability of the omega enzyme donor to conjugate to form catalytically active enzyme complex with an omega enzyme acceptor. Sulfhydryl and amino groups are preferred.

When a free sulfhydryl is present, it can react with a reactive group that is present on the analyte. Such reactive groups include but are not limited to, reactive haloalkyl groups and acid/halo groups, p-mercuribenzoate groups and groups capable of Michael-type addition reactions (including, for example, maleimides and groups of the type described in Mitral and Lawton, 1979, *J. Amer. Chem. Soc.* 101:3097–3110). Haloalkyl as defined herein comprises any alkyl group from one to three carbon atoms substitute with bromine, iodine or chlorine. If the analyte does not possess such reactive group for coupling to the free sulfhydryl of the omega donor, a derivative of the analyte can be prepared to contain such reactive group.

According to another embodiment of the present invention, an omega-enzyme donor polypeptide is prepared by ligating or fusing a gene encoding an omega-donor domain with another gene encoding the protein analyte (or a protein thereof) to be assayed. The expression of the ligated genes in an appropriate host cell results in a fusion protein product that is capable both of complementation with an omega acceptor and specific binding to the analyte-binding protein. Thus, fusion proteins prepared according to this embodiment of the present invention compromise two domains: (1) an omega-donor domain, and (2) a protein domain, both encoded by a fused gene. As mentioned previously, the protein domains utilized in this invention comprise immunoreactive epitopes of protein antigens.

In order to construct a gene which encodes a fusion protein, the two genes in question must be joined with their coding sequences such that the translational reading frame is maintained and is uninterrupted by termination signals. Further, if the host cell is a strain which contains a repressor, the fusion protein will be produced only in response to inactivation of the repressor of induction. The fusion proteins are identified for their complementation activity by in vivo complementation of an omega acceptor. Screening of genetic constructions for immunoreactivity and immunospecific inhibition of complementation by interaction of antibody with the protein domain are accomplished in vitro.

Fusion proteins are normally constructed so that the immunoreactive polypeptide is attached to the C-terminus of the omega-donor domain. A spacer sequence between the omega-donor domain and the protein domain can be used to enhance complementation or to enhance the inhibitory effect of interaction with specific binding protein on complementation.

Further, fusion of an entire gene coding for a particular protein analyte may not be required. For example, the related human glycoproteins leutropin (leuteininzing hormone; LH), follitropin (follicle-stimulating hormone; FSH), thyrotropin (thyroid-stimulating hormone; TSH) and human chorionic gonadotropin (hCG) are comprised of $\alpha$ and $\beta$-subunits. The $\alpha$-subunits of all these hormones are identical. But in each case, the $\beta$-subunit is distinct and confers the unique specificity and biologic activity of each hormone. Thus only the $\beta$-subunit may need to be fused to the omega-donor domain sequence to construct an immunoassay specific for a particular hormone of this group.

Alternatively, the immunoreactive sequence coding for the protein domain which is fused to the omega-donor coding gene sequence could represent a unique immunoreactive epitope. For example, the unique carboxyl-terminal 30 amino acid extension of the $\beta$-subunit of hCG (Birken et al. 1982, *Endocrinolgy* 110:1555) can be used as the protein domain in an assay for hCG.

As another illustrative example, the sequence for the entire Hepatitis B Virus surface antigen or only a small portion of this sequence could be used as the immunoreactive epitope for the Hepatitis B virus (Lernere et al., 1981, *Proc. Natl. Acad. Sci. USA* 78:3403).

As mentioned previously, the constant of association between omega donor and omega acceptor polypeptides is an important parameter for achieving satisfactory sensitivity with any enzyme complementation assay system. According to the embodiments of the present invention, in order to adjust the constant association between omega donor and omega acceptor, the amino acid sequence of either the enzyme-donor omega-domain (see above) or the omega acceptor can be systematically altered.

Omega acceptors with varied affinities for omega donor are prepared using a variety of recombinant DNA techniques including, but not limited to, deletion constructions and direct synthesis of DNA carrying the desired amino acid sequence followed by in-frame ligating into the DNA sequence of the omega-region of the lacZ gene which encodes native $\beta$-galactosidase.

Illustrative techniques for the preparation of omega acceptors by deletion constructions are presented in detail below. Very briefly, deletion construction techniques entail introduction of sites specific for particular restriction enzymes into the omega-region of the $\beta$-galactosidase Z gene, followed by site-specific digestion, e.g., Bal31 digestion, to afford a gene encoding the desired amino acid sequence. After digestion with appropriate restriction enzymes, the viable omega acceptors are isolated using in vivo complementation ability. For example, complementation can be screened by transforming plasmids, bearing thermoinducible genes coding for an omega donor as well as the omega acceptor of interest, into a strain such as AMA1004 (AMA1004 is galU, galK, StrA$^r$, hsdR$^-$, leuB6, trpC, $\Delta$(lacIPOZ)C29 (Casadaban et al., 1983, Methods in Enzymology 100:293) and selecting on plates containing the inducer isopropylthiogalactoside and the chromogenic substrate 5-bromo-4-chloro-3-indolyl-$\infty$-D-galactopyranoside. Colonies that are white at 30° C. but blue at 42° C. indicates the creation of viable omega acceptors. The omega donor DNA sequences are then removed from the plasmid by restrictive enzyme digestion, and the plasmid is then religated and transformed into AMA 1004. The omega acceptor polypeptides are then purified.

Alternatively, the omega acceptors are prepared by direct synthesis of DNA using any commercial DNA synthesizer. The desired synthetic DNA sequence is then annealed and ligated into an appropriate plasmid vector. For example, plasmid p151 is digested with SacI and SalI restriction enzymes. The desired synthetic DNA sequence is then inserted into the SacI/SalI gap.

The improved methods and novel compositions of the present invention can be used to determine the presence and/or quantity of a variety of analytes including drugs and drug metabolites, biologically active molecules, steroids, vitamins, industrial pollutants, pesticides and their metabolites, food additives, herbicides and their metabolites, flavoring agents and food poisons, pathogens and toxins they produce, and other substances of interest. Analytes of relatively high molecular weight, e.g., proteins with MW greater than about 2,000 daltons, as well as small analytes, can be detected and/or measured with the improved assays and compositions of this invention. Illustrative examples of such analytes include, but are not limited to the following:

| HIGH MOLECULAR WEIGHT | LOW MOLECULAR WEIGHT |
|---|---|
| Carcinoembryonic antigen | Estriol |
| Ferritin | Digoxin |
| Human T-Cell Leukemia Virus | Thyroxine |
| Insulin | Propranolol |
| α-fetoprotein | Methotrexate |
| Rubella Virus | Phencyclidine |
| Herpesvirus | Methadone |
| Cytomegalovirus | Morphine |
| Follicle stimulating hormone | Diazepam |
| Thyroid stimulating hormone | Oxazepam |
| Luteinizing hormone | Quinidine |
| Hepatitis Virus | Propoxyphen |
| Chorionic Gonadotropin | N-acetylprocainamide |
| Estrogen receptor | Secobarbital |
| Thyroid stimulating hormone receptor | Tobramycin |
| Poliovirus receptor | Gentamicin |
| Insulin transport protein | Theophylline |
| Protein A | Amphetamine |
| Con A lectin | Benzoyl ecgonine |
| Wheat Germ agglutinin lectin | Phenytoin |
| Secretory protein | Procainamide |
| Cholera toxin | Lidocaine |
| Avidin | Carbamazepine |
|  | Primidene |
|  | Valproic Acid |
|  | Phenobarbital |
|  | Ethosuxinimide |
|  | Biotin |

In the enzyme assays of the present invention, the amount of unknown analyte in a sample mixture is measured as a direct function of the activity of the β-galactosidase enzymes. Enzyme activity is monitored by the appearance of a product of the enzymatically catalyzed reaction or by disappearance of the enzyme substrate. This is the rate of conversion of substrate. Substrates for β-galactosidase that are suitable for spectrophotometric or fluorometric analysis include, but are not limited to: p-aminophenyl-β-D-galactopyranoside; 2'-N-(hexadecanol)-N-(amino-4'-nitrophenyl)-β-D-galactropyranoside; 4-methylumbelliferyl-β-D-galactopyranoside; napthyl-AS0Bl-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galactopyranoside, 5-bromo-4-chloro-3-indolyl-β-D-galactopyranoside, resorufin-β-D-galactopyranoside, 7-hydroxy-4-trifluoromethyl coumarin, and fluorescein-β-galactopyranoside.

The enzyme assays of the present invention utilize competitive interaction for an analyte-binding protein between free analyte and omega-donor conjugate. Interaction of omega-donor conjugate with the analyte-binding protein inhibits the complementation reaction. As described in detail in the examples (infra), attachment of antibody or antibody fragment specific for the analyte-binding protein appears to enhance steric hindrance effects and thus contribute to the inhibition of complementation by the omega-donor conjugate bound to the analyte-binding protein.

According to one embodiment of the present invention, the analyte-binding protein is an antibody molecule. In such case, the assay is an enzyme immunoassay. The antibody molecules useful for such assays include both conventional (polyclonal) and monoclonal antibodies (and fragments of polyclonal or monoclonal antibodies) specific for the analyte to be measured or the recombinant polypeptide fragments capable of specifically binding the analyte.

According to another embodiment of the present invention, the analyte-binding protein is avidin, which has special affinity for biotin. In such case the enzyme assay is useful to measure not only biotin, but derivatives of biotin which retain affinity for avidin.

According to another embodiment of the present invention, the analyte-binding protein is a binding protein including, but not limited to receptors, lectins and transport proteins.

The invention now being generally described, the same will be better understood by reference to the following detailed examples which are presented for purposes of illustration only and are not to be considering limiting of the invention unless so specified.

EXAMPLES

Example 1

Construction of Omega Proteins

1. Omega-Donor Molecule; OD6.

Figure 2:
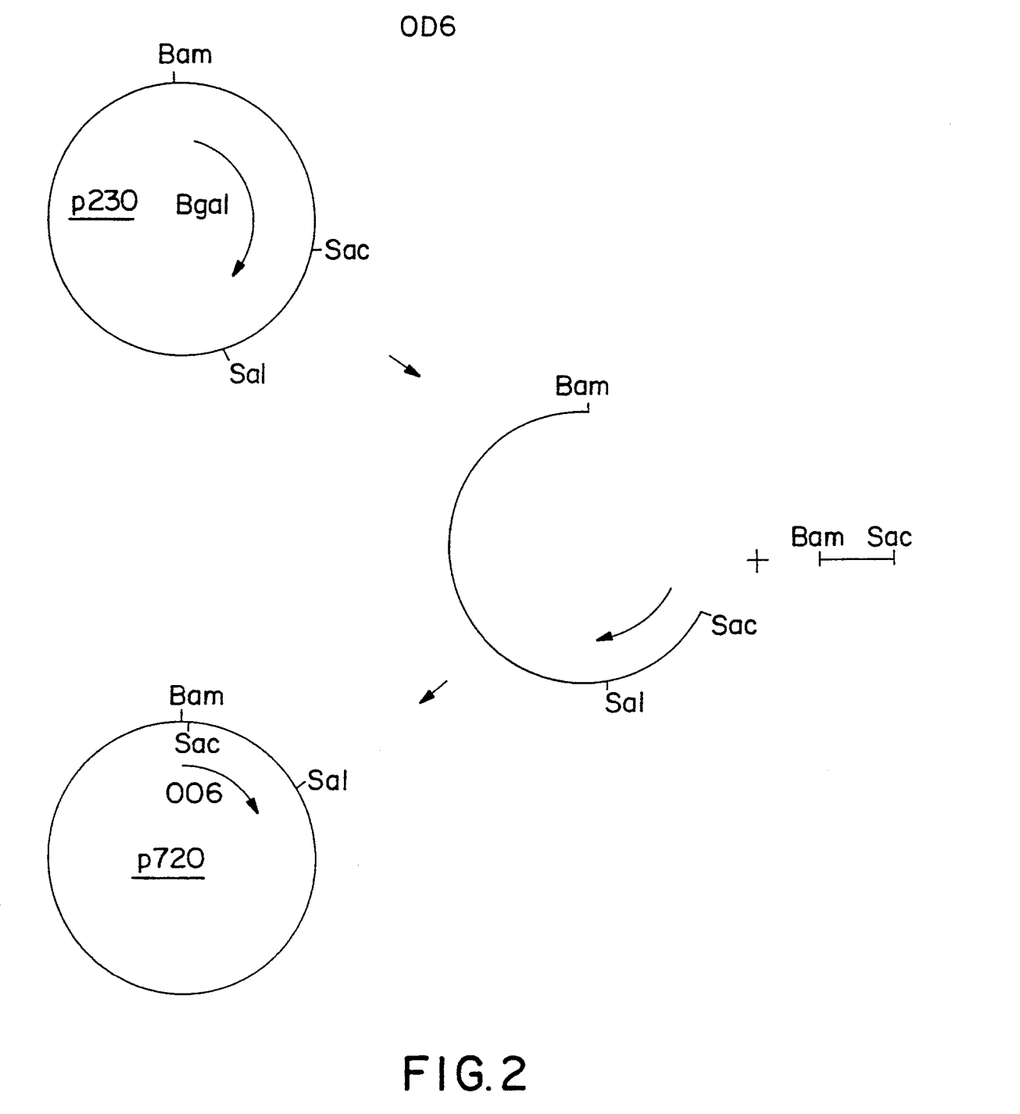
FIG. 2 represents in schematic form the construction of a recombinant plasmid containing an omega donor domain.

An exemplary omega-donor was prepared using standard techniques of genetic engineering as shown schematically in FIG. 2. The carboxyl-terminus one-third of β-galactosidase was produced by removing the first two-thirds of the β-gal DNA sequence from a DNA plasmid containing the sequence of the intact β-galactosidase molecule using a DNA restriction enzyme. Other omega donors can be prepared using other restriction enzymes that cleave at or near the indicated restriction site. In this example, the plasmid P230 was used. However, this plasmid was used merely as a matter of convenience, as other plasmids of known sequence containing a β-galactosidase gene can be used with equal ease. Sources of β-galactosidase genetic material are described elsewhere in this specification.

The plasmid P230 was cleaved with restriction enzymes at the Bam and Sac sites to produce two pieces of DNA. The large piece was isolated by agarose gel electrophoresis. A synthesized DNA linker containing Bam and Sac ends was ligated into the isolated large piece to recircularize the plasmid. The final product contains the carboxyl-terminus one-third of β-galactosidase. The resulting plasmid is referred to herein as P720. Expression of this plasmid in a host bacterial cell produces the OD6 molecule, which has 378 amino acids and a molecular weight of 43,000 daltons.

2. Omega-Acceptor Molecule; OA721

Figure 3:
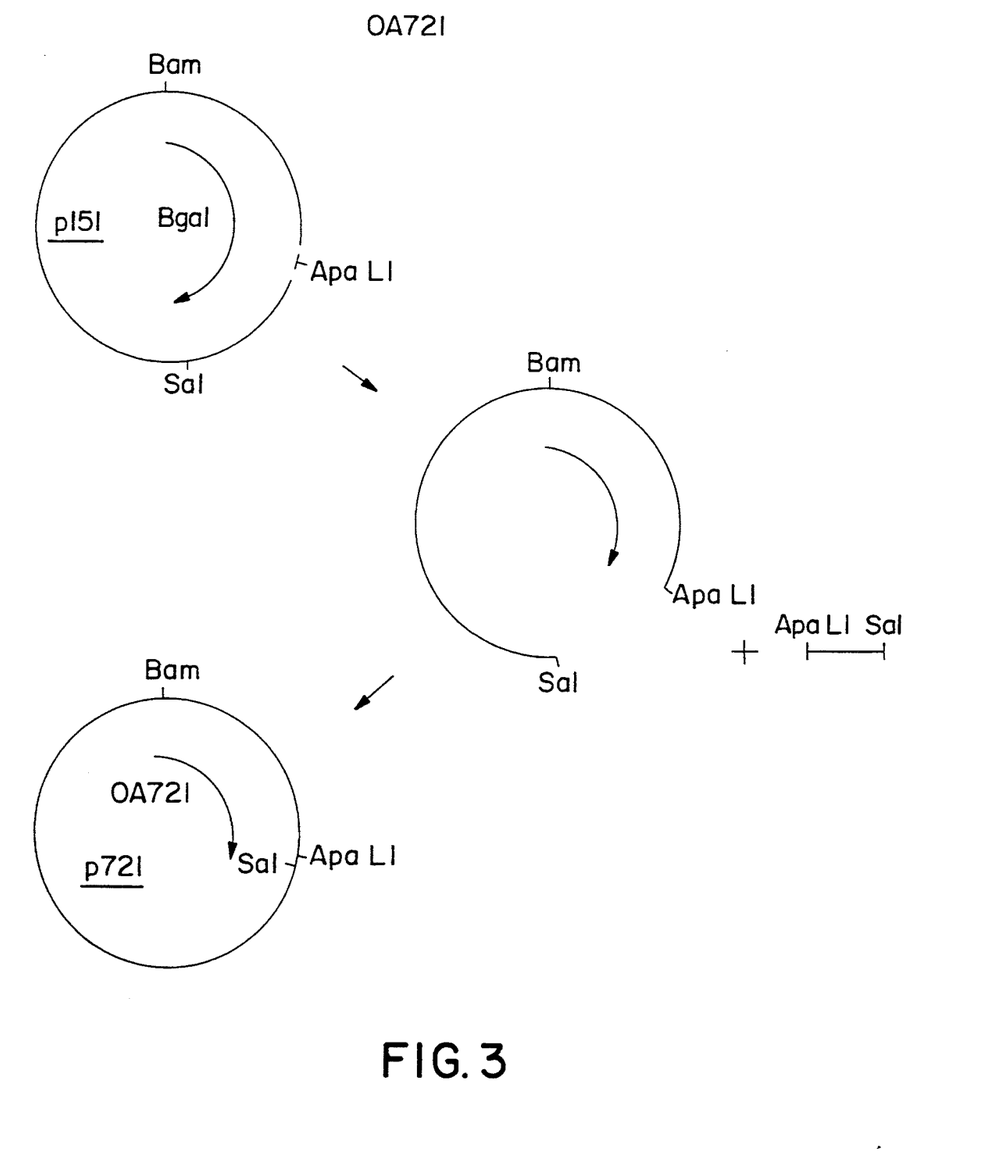
FIG. 3 represents in schematic form the construction of a recombinant plasmid containing an omega acceptor domain.

An exemplary omega acceptor was constructed by removal of the carboxyl terminus DNA sequences from a plasmid containing the sequence of the intact β-galactosidase molecule, leaving a truncated β-galactosidase with 787 amino acids and molecular weight of 94,000 daltons. Construction of the plasmid is shown schematically in FIG. 3. The source plasmid was p151, a different plasmid which also encodes β-galactosidase. The p151 plasmid was digested with enzymes at the ApaLI and Sal sites to produce two pieces of DNA. The large piece was isolated by agarose gel electrophoresis. A synthesized DNA linker containing ApaII and Sal ends was ligated into the isolated large piece to recircularize the plasmid. The final product contains the amino-terminus two-thirds of the β-galactosidase gene. The omega-acceptor molecule, OA721, is missing the final 236 amino acids of β-galactosidase, which can be found within the complementary 378 amino acid omega-donor molecule.

Example 2

Purification of Omega Proteins

1. Omega Donor; OD6

MG720, an *E. coli* strain harboring the plasmid which codes for the OD6 gene, was grown at 30° C. until the cell growth was exponential. When the cell mass reached $OD_{600}=1.0$, the temperature was raised to 42° C., which induces the synthesis of OD6 from a high-temperature inducible promotor. After four hours at 42° C., the cells were collected and frozen. The frozen cells were thawed and lysed in the presence of aqueous buffer and lysozyme. This lysate was cleared by centrifugation, and the pelleted material was extracted for OD6 protein by a series of resuspensions in increasing urea concentrations. The OD6 protein was found in the 8M urea extraction. The 8M urea extract was made 15% saturated with ammonium sulfate, and the precipitate was collected by centrifugation. The precipitate was resuspended into 6M guanidine hydrochloride and dialyzed with several changes into an 8M urea/TRIS HCl pH 7.5 buffer. The dialyzed material was then further dialyzed into an aqueous TRIS HCl pH 7.5 buffer with several changes. The dialyzed OD6 protein extract was then cleared of precipitation by centrifugation, and the cleared extract was made 50% saturated with ammonium sulfate. The precipitate was collected by centrifugation and resuspended into a 0.5 M NaCl/TRIS HCl pH 7.5 buffer and purified using sizing gel chromatography. The active peak was concentrated and stored at 4° C.

2. Omega Acceptor; OA721

OA721 protein (strain MG721) was expressed by the same procedure as outlined above for OD6. After cell lysis, the cell material was cleared by centrifugation. The cleared lysate was made 25% saturated in ammonium sulfate, and the precipitate was stored at a pellet at 4° C. The pellet material was extracted twice with 2M urea buffer, and both cleared lysates were pooled and made 25% in ammonium sulfate. The precipitate was again stored as a pellet at 4° C. The 25%-saturated ammonium sulfate pellet was resuspended into a Tris buffer and purified by ion-exchange chromatography. The active peak, determined by a complementation assay using OD6 protein, was concentrated and stored at 4° C., or −20° C., depending on the batch.

Example 3

Omega Complementation Immunodiagnostic Test

An immunoassay was carried out to detect low concentrations of analyte in patient sera. The analyte chosen for the test was theophylline, which has a therapeutic range of 0–40 μg/ml. The purified OD6 molecule was covalently bound to theophylline in a manner which does not interfere with complementation.

For this purpose, purified OD6 protein was buffer exchanged using a Sephadex G-25 column to remove any β-mercaptoethanol. The activity of OD6 fractions was monitored by assay with OA721. To the pooled OD6 fractions, a solution of a theophylline-maleimide derivative in DMF was added, and the reaction mixture was incubated for 20 minutes at room temperature. The reaction mixture was passed over a Sephadex G-25 column again to remove excess theophylline-maleimide derivative. The OD6-theophylline conjugate was pooled and assayed for complementation activity with OA 721 and for immunochemical binding with anti-theophylline antibody. Assays were performed in microtiter plates at room temperature. OA, OD and substrate were combined at t=0 min. The rates are derived from mAU of substrate turnover measured in 1 min. intervals. No antibody or dose was present in the assay wells.

Figure 4:
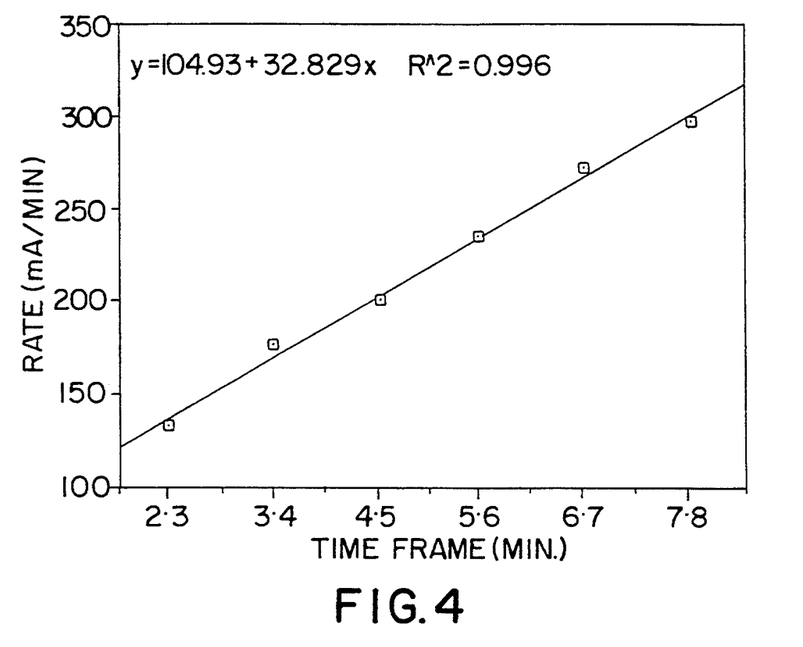
FIG. 4 is a diagram showing omega complementation kinetics.
Figure 5:
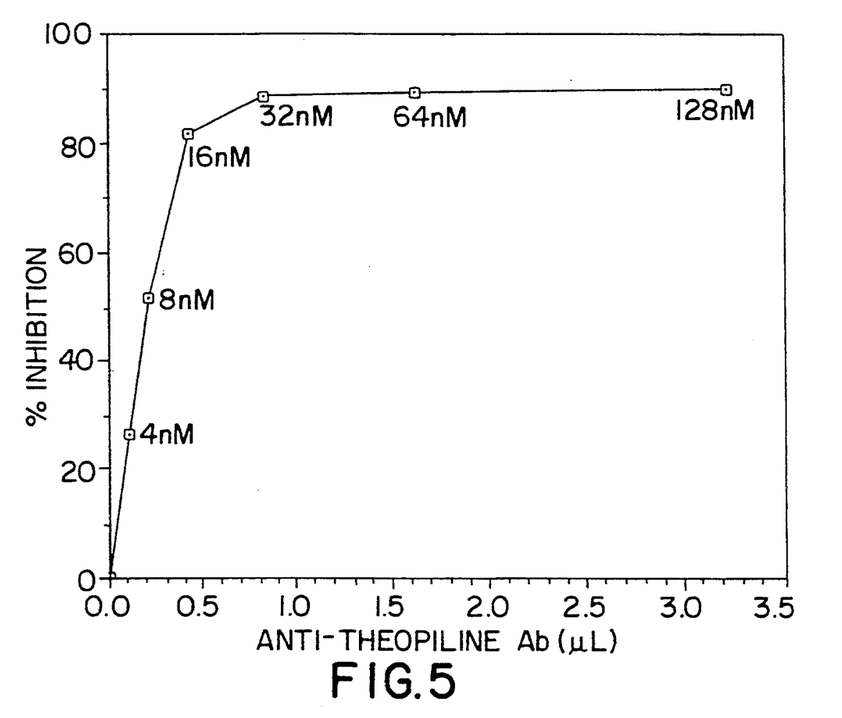
FIG. 5 graphically represents a competitive binding curve for a homogeneous assay for theophylline wherein the analyte-binding protein is an antibody.

FIG. 4 shows a liner increase in substrate turnover versus time for a substrate incubated with the OD6/theophylline conjugate. In the presence of anti-theophylline antibody, however, the complementation of OD6/theophylline conjugate and OA721 is sterically inhibited (FIG. 5) due to binding of the antibody to the covalently bound theophylline. Concentration of antibody binding sites (nM system) are shown beside each data point.

Figure 6:
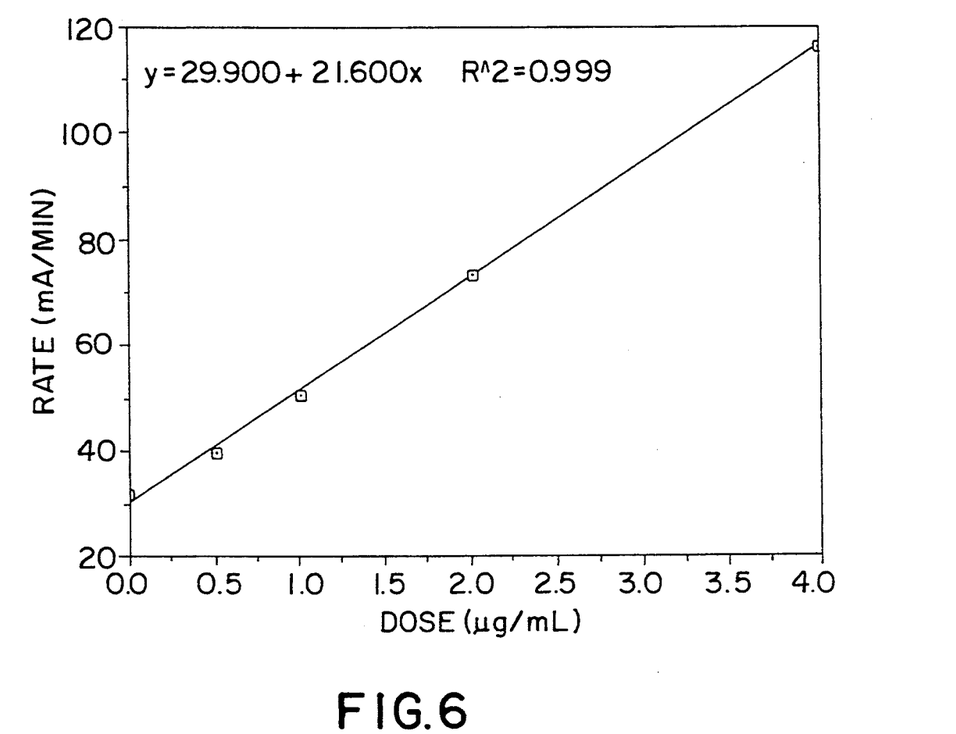
FIG. 6 graphically represents a competitive binding curve (dose response curve) for an assay for theophylline wherein the analyte-binding protein is anti-theophylline antibody.

To further demonstrate the usefulness of this assay, a dose response to free theophylline was investigated. The free theophylline competes for antibody sites, thus freeing OD6/theophylline conjugate for complementation with OA721. Thus, the rate of substrate hydrolysis measured is directly related to the amount of free theophylline present. FIG. 6 shows a linear dose response of theophylline in the omega assay in a range of 0–4 μg/ml when the optical density was measured in the "read frame" of six to eight minutes after the addition of substrate at room temperature. Assays were performed in microtitre plates at room temperature. OD concentration was 4 nM system, antibody binding sites concentration was 8 nM systems. Antibody was first preincubated with dose. OD was then added to this mixture for an additional preincubation. OA and substrate were then added at t=0 min.

All publications and patent applications mentioned in this specification are herein incorporated by reference to the same extent as if each individual publication or patent application was specifically and individually indicated to be incorporated by reference.

The invention now being disclosed in detail and by examples, it will be recognized by one skilled in the art that many modifications and variations of these examples are possible while still falling within the scope of the present invention and the appended claims.

What is claimed is:

1. In an improved β-galactosidase complementation assay method for determining the presence of an analyte in a sample, wherein an inactive donor polypeptide fragment of β-galactosidase and an inactive acceptor polypeptide of β-galactosidase which interact when combined to form an active β-galactosidase enzyme are combined in a reaction solution with said sample and additional reagents required for said complementation assay, an improvement comprising:

utilizing as said inactive donor polypeptide fragment a polypeptide comprising 10 to 500 amino acids of the C-terminus of β-galactosidase and utilizing as said acceptor polypeptide fragment a polypeptide comprising 600 to 1012 amino acids of the N-terminus of β-galactosidase, wherein no gap is present between said donor and acceptor polypeptide sequences when said sequences complement to form said active enzyme and further wherein said donor polypeptide is coupled to an analyte but not at the N-terminus of said donor polypeptide, with the proviso that the combination of X90, a polypeptide comprising β-galactosidase from which the amino acids at position 1013 to position 1023 have been deleted, as said acceptor molecule and CNBr24, a polypeptide containing the amino acids from position 990 to position 1023 of β-galactosidase, as said donor polypeptide is excluded.

2. The method of claim 1, wherein said donor polypeptide comprises 300 to 450 amino acids of the C-terminus of β-galactosidase.

3. The method of claim 1, wherein said acceptor polypeptide comprises 700 to 850 amino acids of the N-terminus of β-galactosidase.

4. In an improved β-galactosidase complementation assay method for determining the presence of an analyte in a sample, wherein an inactive donor polypeptide fragment of β-galactosidase and an inactive acceptor polypeptide of β-galactosidase which interact when combined to form an active β-galactosidase enzyme are combined in a reaction solution with said sample and additional reagents required for said complementation assay, an improvement comprising:
utilizing as said inactive donor polypeptide fragment a polypeptide comprising 300 to 450 amino acids of the C-terminus of β-galactosidase and utilizing as said acceptor polypeptide fragment a polypeptide comprising 700 to 850 amino acids of the N-terminus of β-galactosidase, wherein no gap is present between said donor and acceptor polypeptide sequences when said sequences complement to form said active enzyme and further wherein said donor polypeptide is coupled to an analyte but not at the N-terminus of said donor polypeptide, with the proviso that the combination of X90, a polypeptide comprising β-galactosidase from which the amino acids at position 1013 to position 1023 have been deleted, as said acceptor molecule and CNBr24, a polypeptide containing the amino acids from position 990 to position 1023 of β-galactosidase, as said donor polypeptide is excluded.

5. In an improved β-galactosidase complementation assay method for determining the presence of an analyte in a sample, wherein an inactive donor polypeptide fragment of β-galactosidase and an inactive acceptor polypeptide of β-galactosidase which interact when combined to form an active β-galactosidase enzyme are combined in a reaction solution with said sample and additional reagents required for said complementation assay, an improvement comprising:
utilizing as said inactive donor polypeptide fragment a polypeptide comprising 378 amino acids of the C-terminus of β-galactosidase and utilizing as said acceptor polypeptide fragment a polypeptide comprising 787 amino acids of the N-terminus of β-galactosidase, wherein no gap is present between said donor and acceptor polypeptide sequences when said sequences complement to form said active enzyme and further wherein said donor polypeptide is coupled to an analyte but not at the N-terminus of said donor polypeptide, with the proviso that the combination of X90, a polypeptide comprising β-galactosidase from which the amino acids at position 1013 to position 1023 have been deleted, as said acceptor molecule and CNBr24, a polypeptide containing the amino acids from position 990 to, position 1023 of β-galactosidase, as said donor polypeptide is excluded.

6. In an enzyme complementation assay for determining the presence or concentration of a suspected analyte in a sample, which comprises the steps of: (1) combining in a reaction solution (a) an enzyme-donor polypeptide and an enzyme-acceptor polypeptide from β-galactosidase, both of which are enzymatically inactive when separate but which interact when combined to form an active β-galactosidase enzyme, (b) said sample, and (c) additional reagents required for said complementation assay, and (2) measuring β-galactosidase activity in said reaction, an improvement which comprises:
utilizing as said donor polypeptide a polypeptide having an amino acid sequence substantially identical to 300 to 450 amino acids located at the carboxyl terminus of β-galactosidase and utilizing as said enzyme acceptor polypeptide a polypeptide having an amino acid sequence substantially identical to 700 to 850 amino acids located at the amino terminus of β-galactosidase, wherein no gap is present between said donor and acceptor polypeptide sequences when said sequences complement to form said active enzyme, with the proviso that the combination of X90, a polypeptide comprising β-galactosidase from which the amino acids at position 1013 to position 1023 have been deleted, as said acceptor polypeptide and CNBr24, a polypeptide containing the amino acids from position 990 to position 1023 of β-galactosidase, as said donor polypeptide is excluded, and further wherein said donor polypeptide comprises an analyte coupling domain not attached to the N-terminus of said donor polypeptide.

7. In an enzyme complementation assay for determining the presence or concentration of a suspected analyte in a sample, which comprises the steps of: (1) combining in a reaction solution (a) an enzyme-donor polypeptide and an enzyme-acceptor polypeptide from β-galactosidase, both of which are enzymatically inactive when separate but which interact when combined to form an active β-galactosidase enzyme, (b) said sample, and (c) additional reagents required for said complementation assay, and (2) measuring β-galactosidase activity in said reaction, an improvement which comprises;
utilizing as said donor polypeptide a polypeptide having an amino acid sequence substantially identical to 300 to 450 amino acids located at the carboxyl terminus of β-galactosidase and utilizing as said enzyme acceptor polypeptide a polypeptide having an amino acid sequence substantially identical to 700 to 850 amino acids located at the amino terminus of β-galactosidase, wherein no gap is present between said donor and acceptor polypeptide sequences when said sequences complement to form said active enzyme, with the proviso that the combination of X90, a polypeptide comprising β-galactosidase from which the amino acids at position 1013 to position 1023 have been deleted, as said acceptor polypeptide and CNBr24, a polypeptide containing the amino acids from position 990 to position 1023 of β-galactosidase, as said donor polypeptide is excluded, and further wherein said donor polypeptide comprises an analyte coupling domain substantially removed from the N-terminus of said donor polypeptide.

8. In an enzyme complementation assay for determining the presence or concentration of a suspected analyte in a sample, which comprises the steps of: (1) combining in a reaction solution (a) an enzyme-donor polypeptide and an enzyme-acceptor polypeptide from β-galactosidase, both of which are enzymatically inactive when separate but which interact when combined to form an active β-galactosidase enzyme, (b) said sample, and (c) additional reagents required for said complementation assay, and (2) measuring β-galactosidase activity in said reaction, an improvement which comprises:

utilizing as said donor polypeptide a polypeptide having an amino acid sequence substantially identical to 300 to 450 amino acids located at the carboxyl terminus of β-galactosidase and utilizing as said enzyme acceptor polypeptide a polypeptide having an amino acid sequence substantially identical to 700 to 850 amino acids located at the amino terminus of β-galactosidase, wherein no gap is present between said donor and acceptor polypeptide sequences when said sequences complement to form said active enzyme, with the proviso that the combination of X90, a polypeptide comprising β-galactosidase from which the amino acids at position 1013 to position 1023 have been deleted, as said acceptor polypeptide and CNBr24, a polypeptide containing the amino acids from 990 to position 1023 of β-galactosidase, as said donor polypeptide is exclude, and further wherein said donor polypeptide comprises an analyte coupling domain located at the C-terminus of said donor polypeptide.

* * * * *